United States Patent
Fujii et al.

(10) Patent No.: US 8,178,148 B2
(45) Date of Patent: May 15, 2012

(54) COFFEE DRINK COMPOSITION

(75) Inventors: Akihiko Fujii, Haga-gun (JP); Atsushi Suzuki, Haga-gun (JP); Hideo Oominami, Haga-gun (JP); Ryuji Ochiai, Haga-gun (JP); Yusuke Shibuya, Haga-gun (JP)

(73) Assignee: Kao Corporation, Tokyo (JP)

( * ) Notice: Subject to any disclaimer, the term of this patent is extended or adjusted under 35 U.S.C. 154(b) by 1343 days.

(21) Appl. No.: 10/586,609

(22) PCT Filed: Jan. 27, 2005

(86) PCT No.: PCT/JP2005/001074
§ 371 (c)(1),
(2), (4) Date: Jul. 19, 2006

(87) PCT Pub. No.: WO2005/072533
PCT Pub. Date: Aug. 11, 2005

(65) Prior Publication Data
US 2007/0160726 A1    Jul. 12, 2007

(30) Foreign Application Priority Data

Jan. 30, 2004   (JP) ................................. 2004-024247
Dec. 28, 2004   (JP) ................................. 2004-380614

(51) Int. Cl.
A23F 5/00    (2006.01)
(52) U.S. Cl. ......... 426/422; 426/594; 426/595; 426/106
(58) Field of Classification Search .................. None
See application file for complete search history.

(56) References Cited

U.S. PATENT DOCUMENTS

| 2,430,663 | A | * | 11/1947 | Behrman | ....................... 426/124 |
| 3,615,666 | A | * | 10/1971 | Schlichter et al. | ............ 426/386 |
| 5,087,469 | A | | 2/1992 | Acree | |
| 5,558,742 | A | * | 9/1996 | Kiefer | ....................... 156/244.16 |
| 6,894,077 | B2 | | 5/2005 | Suzuki et al. | |
| 7,534,815 | B2 | | 5/2009 | Suzuki et al. | |
| 2004/0005398 | A1 | * | 1/2004 | Slaga et al. | ................... 426/595 |

FOREIGN PATENT DOCUMENTS

| EP | 1 186 294 A2 | 3/2002 |
| EP | 1 264 596 A2 | 12/2002 |
| GB | 354942 | * 8/1931 |
| JP | 57-28089 | 2/1982 |
| JP | 4-360647 | 12/1992 |
| JP | 5-111437 | 5/1993 |
| JP | 6-315434 | 11/1994 |

(Continued)

OTHER PUBLICATIONS

U.S. Appl. No. 10/587,258, filed Jul. 26, 2006, Fujii, et al.

(Continued)

*Primary Examiner* — Humera Sheikh
*Assistant Examiner* — Felicia King
(74) *Attorney, Agent, or Firm* — Oblon, Spivak, McClelland, Maier & Neustadt, L.L.P.

(57) ABSTRACT

Provided is a coffee composition having an excellent hypotensive effect. The coffee composition has the following components (A) and (B):
  0.01 to 1 wt. % of chlorogenic acids (A),
  less than 0.1 wt. %, based on the weight of the chlorogenic acids, of (B) hydroxyhydroquinone.

17 Claims, 5 Drawing Sheets

Retention time (min)

FOREIGN PATENT DOCUMENTS

| JP | 7-313063 | 12/1995 |
|---|---|---|
| JP | 2002-53464 | 2/2002 |
| JP | 2002-87977 | 3/2002 |
| JP | 2002-363075 | 12/2002 |
| JP | 2003-304812 | 10/2003 |

OTHER PUBLICATIONS

Darby & Darby Mar. 25, 2009 letter, received by Applicants' representative Mar. 26, 2009.

Jeanne B. Martin, et al., "Mortality Patterns Among Hypertensives by Reported Level of Caffeine Consumption", Preventative Medicine 17, (1988), pp. 310-320.

Richard H. Adamson, "Evaluation of Coffee and Caffeine for Mutagenic, Carcinogenic, and Anticarcinogenic Activity", American Chemical Society 2000, Chapter 9, pp. 71-77.

M-L Nurminen[1], et al., "Coffee, caffeine and blood pressure: a critical review", European Journal of Clinical Nutrition, vol. 53, No. 11, 1999, pp. 831-839.

* cited by examiner

COFFEE DRINK COMPOSITION

FIELD OF THE INVENTION

The present invention relates to a coffee composition having an antihypertensive effect.

BACKGROUND OF THE INVENTION

Examples of antihypertensive drugs include various neuroleptic drugs having effective actions on the neural-factor-related regulatory system, ACE inhibitors having effective actions on the neurohumoral-factor-related regulatory system, AT receptor antagonists, Ca antagonists associated with the vascular-endothelium-derived-substance-related regulatory system, and hypotensive diuretics associated with the body-fluid-regulatory system in the kidney. Under the present circumstances, however, any pharmaceutical drug used for treatment of hypertension imposes a serious burden on patients, because its side effects cannot be lightly ignored notwithstanding its satisfactory effectiveness is acknowledged.

General therapies for improving the life style such as diet therapy, kinesitherapy, and limitation of alcoholic intake or smoking are applied widely not only to patients having a high normal blood pressure including a mild case, but also to patients suffering from severe hypertension. With growing awareness of the importance of general therapies, improvement of eating habits is becoming especially important. There are a number of foods having an antihypertensive effect. Blood pressure lowering materials derived from foods have so far been searched extensively and a number of effective ingredients have been isolated from them or identified.

It is reported that, of such effective ingredients, chlorogenic acid, caffeic acid, ferulic acid and the like contained in foods such as coffee have an excellent antihypertensive effect (Patent Documents 1 to 3). On the other hand, there is a report indicating that a coffee beverage known to contain a large amount of chlorogenic acids was not recognized to have a clear hypotensive effect and rather increased the blood pressure level (Non-patent Document 1).

Patent Document 1:JP-A-2002-363075
Patent Document 2:JP-A-2002-22062
Patent Document 3:JP-A-2002-53464
Non-patent Document: Eur. J. Clin. Nutr., 53(11), 831(1999)

DISCLOSURE OF THE INVENTION

In one aspect of the present invention, there are thus provided a coffee composition containing the following components (A) and (B):

from 0.01 to 1 wt. % of (A) chlorogenic acids,
less than 0.1 wt. %, based on the chlorogenic acids, of (B) hydroxyhydroquinone; and a process for preparing the coffee composition.

In another aspect of the present invention, there are also provided a soluble coffee composition containing the following components (A) and (B):

from 0.1 to 10 wt. % of (A) chlorogenic acids,
less than 0.1 wt. %, based on the chlorogenic acids, of (B) hydroxyhydroquinone; and a process for preparing the soluble coffee composition.

In a further aspect of the present invention, there is also provided a packaged beverage having, filled therein, a coffee composition containing the following components (A) and (B):

from 0.01 to 1 wt. % of (A) chlorogenic acids,
less than 0.1 wt. %, based on the chlorogenic acids, of (B) hydroxyhydroquinone.

In a still further aspect of the present invention, there are also provided a coffee composition containing from 0.01 to 1 wt. % of chlorogenic acids, characterized in that in the analysis by high performance liquid chromatography, the composition has no substantial peak within a range of a relative retention time of from 0.54 to 0.61 with respect to gallic acid used as a reference substance; a process for preparing the composition; and a packaged beverage having the composition filled therein.

In a still further aspect of the present invention, there are also provided a soluble coffee composition comprising from 0.1 to 10 wt. % of chlorogenic acids, characterized in that in the analysis by high performance liquid chromatography, the composition has no substantial peak within a range of a relative retention time of from 0.54 to 0.61 with respect to gallic acid used as a reference substance; and a process for preparing the composition.

MODE FOR CARRYING OUT THE INVENTION

An object of the present invention is to provide a food or beverage having excellent effect for alleviating hypertension and can be taken daily.

Paying attention to the fact that a coffee drink does not exhibit a sufficient hypotensive effect in spite of containing chlorogenic acids, the present inventors have carried out various investigations on the relationship between an antihypertensive effect and components of a coffee drink. As a result, it has been found that hydroxyhydroquinone contained in the coffee drink disturbs the hypotensive effect of chlorogenic acids. As a result of further investigation, it has also been found that a coffee composition having an excellent hypotensive effect is available by keeping the content of chlorogenic acids in the coffee drink within a predetermined range and reducing the hydroxyhydroquinone content to not greater than a predetermined amount which is sufficiently smaller than the ordinary content.

The coffee composition of the present invention has an excellent hypertension alleviating effect, in other words, blood pressure reducing effect or blood pressure rise suppressing effect and can be taken for a long period of time.

Accordingly, the coffee composition of the present invention is useful as a medicament for alleviating hypertension or a food with a label indicating that this food is effective for reducing blood pressure or suppressing a rise in blood pressure, or this food is effective for those having higher blood pressure.

The coffee composition of the present invention contains from 0.01 to 1 wt. %, preferably from 0.05 to 1 wt. %, more preferably from 0.1 to 1 wt. % of (A) chlorogenic acids from the standpoints of an antihypertensive effect, a blood pressure rise suppressing effect and taste. The soluble coffee composition of the present invention contains from 0.1 to 10 wt. %, preferably from 0.5 to 10 wt. %, more preferably from 1 to 10 wt. % of chlorogenic acids. The composition contains, as the chlorogenic acids (A), ($A^1$) monocaffeoylquinic acid, ($A^2$) feruloylquinic acid, and ($A^3$) dicaffeoylquinic acid. As the monocaffeoylquinic acid ($A^1$), usable is at least one selected from 3-caffeoylquinic acid, 4-caffeoylquinic acid and 5-caffeoylquinic acid. As the feruloylquinic acid ($A^2$), usable is at least one selected from 3-feruloylquinic acid, 4-feruloylquinic acid and 5-feruloylquinic acid. As the dicaffeoylquinic acid ($A^3$), usable is at least one selected from 3,4-dicaffeoylquinic acid, 3,5-dicaffeoylquinic acid and 4,5-dicaffeoylquinic acid. The content of the chlorogenic acids can be measured by high performance liquid chromatography (HPLC). A commonly employed detection means in HPLC is UV detection, but higher sensitive detection can be attained using CL (chemiluminescence) detection, EC (electrochemical) detection or LC-Mass detection.

The coffee composition or soluble coffee composition according to the present invention contains less than 0.1 wt. % of hydroxyhydroquinone (B) relative to the amount of the chlorogenic acids. When the amount of hydroxyhydroquinone relative to the chlorogenic acids is less than 0.1 wt. %, the hypotensive effect of the chlorogenic acids can be exhibited fully. The hydroxyhydroquinone content is preferably not greater than 0.03 wt. %, especially preferably not greater than 0.01 wt. %. When the hydroxyhydroquinone amount relative to the chlorogenic acids is not greater than 0.01 wt. %, the hypotensive effect of the chlorogenic acids is not disturbed at all. The hydroxyhydroquinone content in the composition of the present invention may be 0.

The hydroxyhydroquinone content can be measured by high performance liquid chromatography (HPLC). UV detection is commonly employed as a detection means for HPLC, but higher sensitive detection can be attained using CL (chemiluminescence) detection, EC (electrochemical) detection or LC-Mass detection. The measurement of the hydroxyhydroquinone content by HPLC may be carried out after the coffee beverage is concentrated.

Although the hydroxyhydroquinone content can be measured directly by HPLC, it can be determined by concentrating hydroxyhydroquinone of the coffee composition or soluble coffee composition by chromatography of every kind and then measuring the amount of the concentrated fraction. In the case of a packaged beverage, it is preferred to measure the amounts of chlorogenic acids and hydroxyhydroquinone after adding, for example, 0.1N hydrochloric acid to the beverage to prepare an acid solution having a pH of 3 or less just after the package is opened.

The coffee composition or soluble coffee composition of the present invention preferably contains ordinarily contained coffee components except that it has a reduced hydroxyhydroquinone content.

The coffee composition of the present invention preferably contains from 30 to 300 mg/100 g, more preferably from 40 to 250 mg/100 g, especially preferably from 50 to 200 mg/100 g of potassium based on 100 g of the coffee composition. The soluble coffee composition of the present invention preferably contains from 20 to 200 mg/1 g, more preferably from 30 to 180 mg/1 g, even more preferably from 40 to 150 mg/1 g of potassium, each based on 1 g of the soluble coffee composition, from the viewpoint of the taste which coffee originally has. In order to keep the potassium content to fall within the above-described range, it is preferred not to remove potassium positively during the preparation of the coffee composition.

The coffee composition of the present invention has preferably an ash content of 280 mg or less, more preferably 250 mg or less, still more preferably 220 mg or less, yet still more preferably 200 mg or less, each based on 100 g of the coffee composition, from the viewpoint of the taste which coffee originally has. The ash content can be measured in accordance with the method as described in STANDARD TABLES OF FOOD COMPOSITION IN JAPAN Fourth Revised and Enlarged Edition (p28, published in 1982, edited by Resources Review Commission/THE SCIENCE AND TECHNOLOGY AGENCY OF JAPAN), more specifically, by heating at 550° C. and continuing ashing until the residual carbon is disappeared to obtain a constant weight. In order to keep the ash content to fall within the above-described range, it is preferred not to carry out an operation which may increase the ash content during the preparation steps of the coffee composition, for example, an operation of treating with a strong alkali and then returning the pH to a neutral region with an acid.

The coffee composition of the present invention preferably has an $H_2O_2$ (hydrogen peroxide) content preferably not greater than 1 ppm, more preferably not greater than 0.1 ppm, even more preferably not greater than 0.01 ppm from the viewpoint of the taste which coffee originally has. The hydrogen peroxide content can be measured using an ordinarily employed hydrogen peroxide meter, for example, a high sensitivity hydrogen peroxide meter "SUPER ORITECTOR MODEL 5" of Central Kagaku Co.

Although no particular limitation is imposed on the kinds of coffee beans to be used for the coffee composition of the present invention, Brazil, Columbia, Tanzania, Mocha and the like can be used for example. The coffee has following species, that is, Arabica and Robusta. As coffee beans, either one kind or a blend of two or more kinds may be used. No particular limitation is imposed on the roasting method of coffee beans or roasting environment including roasting temperature and ordinary methods can be employed. In addition, no limitation is imposed on an extraction method from the beans. The extraction is carried out, for example, by extracting roasted or roasted and ground coffee beans with water (from 0 to 100° C.) for 10 seconds to 30 minutes. Examples of the extraction method include boiling system, espresso system, siphon system, and dripping system (through paper, flannel or the like).

The term "coffee composition" as used herein means a drink composition using 1 g or greater, preferably 2.5 g or greater, more preferably 5 g or greater of coffee beans in terms of raw beans, per 100 g of the composition. When the coffee composition of the present invention is provided as a packaged beverage, it is preferably single strength. The term "single strength" as used herein means a drink which can be taken without dilution under an ordinary state after the packaged beverage is opened.

The coffee composition or soluble coffee composition of the present invention is available by treating the extract of roasted coffee beans with an adsorbent to reduce its hydroxyhydroquinone content. Examples of the adsorbent include activated carbon and reversed phase carrier. More specifically, the composition is available by adding the adsorbent to the extract of roasted coffee beans or an aqueous solution of the dried extract of roasted coffee beans, stirring the resulting mixture at from 0 to 100° C. for 10 minutes to 5 hours and then removing the adsorbent. The activated carbon or reversed phase carrier serving as the adsorbent is preferably added in an amount of 0.02 to 1.0 time or 2 to 100 times, respectively, each based on the weight of the roasted coffee beans. The activated carbon has an average pore size, in a micropore region, of 5 angstrom (Å) or less, more preferably from 2 to 5 angstrom, even more preferably from 3 to 5 angstrom. In the present invention, the average pore size in the micropore region can be measured by the MP method (adopted by Sumika Chemical Analysis Service, Ltd. and Toray Research Center, Inc.) as described in a document (Colloid and Interface Sc., 26, 46(1968)). As the kind of the activated carbon, coconut shell activated carbon is preferred, with coconut shell activated carbon activated by steam being more preferred. Examples of the commercially available activated carbon include "Shirasagi $WH_2c$" (product of Japan EnviroChemicals, Ltd.), "Taiko CW" (product of Futamura Chemical Co., Ltd.), and "KURARAYCOAL GW" (product of KURARAY CHEMICAL CO., LTD). Examples of the reversed phase carrier include "YMC-ODS-A" (product of YMC Co., Ltd.) and C18 (product of GL Sciences, Inc).

Among them, the treatment using activated carbon as the adsorbent is preferred because it can reduce the hydroxyhydroquinone content selectively without reducing the chlorogenic acid content, is industrially advantageous and moreover, does not reduce the potassium content (the ⅕ or greater, more preferably ½ or greater, based on the weight ratio, of the potassium content is maintained).

The activated carbon obtained by the steam activation exhibits an excellent effect for selectively reducing the hydroxyhydroquinone content without reducing the chlorogenic acid content. Described specifically, when the extract of roasted coffee beans containing from 0.01 to 1 wt. % of chlorogenic acids and containing hydroxyhydroquinone in an amount of 5 wt. % or greater based on the chlorogenic acid amount is used as a raw material, a coffee composition having a reduced hydroxyhydroquinone content can be obtained efficiently. In particular, the treatment with it makes it possible to prepare a coffee composition having a chlorogenic acid content of 80% or greater, moreover 90% or greater, based on that in the raw material, and at the same time, having a reduced hydroxyhydroquinone content.

The hydroxyhydroquinone content in the coffee composition or soluble coffee composition of the present invention can be detected by high performance liquid chromatography as a peak within a range of relative retention time of from 0.54 to 0.61 with respect to gallic acid used as a reference substance. Accordingly, the coffee composition of the present invention can be defined as a coffee composition containing from 0.01 to 1 wt. % of chlorogenic acids, characterized in that the composition has, in the analysis by high performance liquid chromatography, no substantial peak within a range of a relative retention time of from 0.54 to 0.61 with respect to gallic acid employed as a reference substance. The soluble coffee composition of the present invention can be defined as a soluble coffee composition containing from 0.1 to 10 wt. % of chlorogenic acids, characterized in that the composition has no substantial peak within a range of a relative retention time of from 0.54 to 0.61 with respect to gallic acid employed as a reference substance. The analysis by high performance liquid chromatography in the above definition is carried out under analysis conditions B described later.

In order to confirm that the coffee composition of the present invention has no substantial peak within a range of a relative retention time of from 0.54 to 0.61 with respect to gallic acid employed as a reference substance, conventional HPLC can be used. For example, it can be confirmed by the detection using gradient elution with a 0.05M aqueous acetic acid solution and a 0.05M acetic acid 100% acetonitrile solution as eluents, an ODS column and an ultraviolet absorptiometer or the like.

"The composition of the present invention has no substantial peak within a range of a relative retention time of from 0.54 to 0.61 with respect to gallic acid employed as a reference substance" means that the following equation holds: $S2/S1<0.01$ in which S1 represents a peak area of a 1 ppm solution of gallic acid at the time of analysis and S2 represents the sum of peak areas derived from components eluted in the above specified region when the coffee composition is analyzed under the same conditions.

The coffee composition of the present invention may contain sugar such as sucrose, glucose, fructose, xylose, high-fructose corn syrup and sugar alcohol, milk constituent, antioxidant, pH regulator, emulsifier and flavor as desired. Examples of the milk constituent include raw milk, whole milk, powdered whole milk, skimmed milk powder, dairy cream, concentrated milk, skimmed milk, partially skimmed milk and condensed milk. The coffee composition of the present invention preferably has a pH of from 3 to 7.5, more preferably from 4 to 7, even more preferably from 5 to 7 from the viewpoint of the stability of the composition.

The term "soluble coffee composition" means powdered food such as instant coffee powder and the like. The instant coffee powder can be prepared in a conventional manner. For example, it can be prepared by spray drying, that is, spraying a coffee extract from a nozzle and dropping it in a hot wind of about 210 to 310° C., thereby forming porous and water soluble coffee powder; or freeze drying, that is, freezing a coffee extract by using liquid nitrogen or refrigerator, grinding the frozen coffee extract, shifting the resulting particles, and sublimating water under vacuum to reduce the water content to 3% or less.

The coffee composition or soluble coffee composition of the present invention can be filled in a container such as PET bottle, can (aluminum or steel), paper, retort pouch, or bottle (glass) and provided as a packaged beverage. In this case, a 50 to 2500-mL packaged beverage is available by filling the coffee composition of the present invention as is in such a container. The soluble coffee composition of the present invention can be taken after dissolving it in from 25 to 500 mL/g of water or hot water. The packaged beverage has preferably a pH of from 5 to 7.5, especially preferably from 5.4 to 7. As the composition ratio of the monocaffeoylquinic acids in the packaged beverage, a 4-caffeoylquinic acid/3-caffeoylquinic acid weight ratio is preferably from 0.6 to 1.2 and a 5-caffeoylquinic acid/3-caffeoylquinic acid weight ratio is preferably from 0.01 to 3. As the container, an oxygen impermeable container is preferred for preventing the deterioration of the components in the coffee. For example, can such as aluminum can or steel can or bottle made of glass is preferred. The term "can" or "bottle" also means a reseal-type can or bottle that may be recapped for successive use. The term "oxygen impermeable container" as used herein means that the container has oxygen permeability (cc·mm/m$^2$·day·atom) of preferably 5 or less, more preferably 3 or less, even more preferably 1 or less.

Preparation of packaged beverages usually needs sterilization treatment. After the beverage is filled in a container such as metal can, the container having the beverage therein is then sterilized under conditions as specified by Food Sanitation Law if it can withstand heat sterilization. When the container cannot withstand retort sterilization, for example, a PET bottle or paper container, employed is a method of sterilizing the beverage under similar sterilization conditions to those specified by Food Sanitation Law, for example, subjecting the beverage to high-temperature short-time sterilization on a plate type heat exchanger, cooling it to a predetermined temperature and then, filling it in the container. Or, it is possible to sterilize the beverage by heating under sterile conditions and adjust the pH to neutral again under sterile conditions; or to sterilize the beverage by heating under neutral conditions and adjust the pH to acidic again under sterile conditions.

The coffee composition or soluble coffee composition of the present invention contains chlorogenic acids in an amount effective for alleviating hypertension and at the same time has a reduced amount of hydroxyhydroquinone which disturbs the hypertension alleviating effect of the chlorogenic acids so that it is useful as a blood pressure lowering or blood pressure rise suppressing pharmaceutical composition, blood pressure lowering beverage or blood pressure rise suppressing beverage. It is also useful as a beverage with a label indicating that this beverage is used for reducing blood pressure or suppressing a blood pressure rise, or this beverage is effective for those having a higher blood pressure.

EXAMPLES

Example 1

(a) The coffee composition of the present invention was prepared in the following manner. Instant coffee ("NESCAFFEE CAFEINLESS", 2.5 g) was applied to a column filled with 500 g of an ODS filler (octadecylsilylated silica gel) ("YMC TGEL ODS-A" having a pore size of 6 nm and average particle size of 150 μm), followed by elution of a hydroxyhydroquinone-containing fraction with 6 L of a 0.5% aqueous acetic acid solution and elution of a fraction containing chlorogenic acids and the other components with 6 L of methanol. From the fraction A containing chlorogenic acids and the other components, methanol was removed completely by the freeze drying method. From 2.5 g of the instant coffee, 0.933 g of the fraction A was obtained.

(b) The chlorogenic acids and hydroxyhydroquinone in the coffee composition were analyzed in the following manner. The analysis conditions described below are designated as analysis conditions A. As the analytical instrument, HPLC (product of Shimadzu Corporation) was employed. Each component for the HPLC has the following model number: detector: "SPD-M10A", oven: "CTO-10AC", pump: "LC-10AD", autosampler: "SIL-10AD", and column: "Inertsil ODS-2" 4.6 mm in inner diameter×250 mm in length.

The analysis conditions are as follows: sample injection amount: 10 μL, flow rate: 1.0 mL/min, detection wavelength of UV absorptiometer: 325 nm (chlorogenic acids), 290 nm (hydroxyhydroquinone), eluent A: 0.05M acetic acid 3% acetonitrile solution, eluent B: 0.05M acetic acid 100% acetonitrile solution.

Concentration Gradient Conditions

| Time | Eluent A | Eluent B |
| --- | --- | --- |
| 0 minute | 100% | 0% |
| 20 minutes | 80% | 20% |
| 35 minutes | 80% | 20% |
| 45 minutes | 0% | 100% |
| 60 minutes | 0% | 100% |
| 70 minutes | 100% | 0% |
| 120 minutes | 100% | 0% |

The retention times (unit: min) of chlorogenic acids: ($A^1$) monocaffeoylquinic acid: three points of 17.9, 20.4 and 22.0; ($A^2$) feruloylquinic acid: three points of 22.8, 25.8 and 27.0, and ($A^3$) dicaffeoylquinic acid: three points of 32.3, 33.0 and 35.8. From the area found here, the content (wt. %) of the chlorogenic acids was determined using 5-caffeoylquinic acid as a standard substance.

The retention time of hydroxyhydroquinone: 5.5 minutes. From the area found here, the hydroxyhydroquinone content (wt. %) was determined using hydroxyhydroquinone as a standard substance.

The hydroxyhydroquinone content in the coffee composition can also be determined by the below-described analysis method. The following analysis conditions are design as analysis conditions B. As an analytical instrument, HPLC (product of Hitachi, Ltd.) was employed. Each component for the HPLC has the following model number: detector: L-7455, oven: L-7300, pump: L-7100, autosampler: L-7200, column: Inertsil ODS-2 having 4.6 mm in inner diameter×250 mm in length.

The analysis conditions are as follows: sample amount: 10 μL, flow rate: 1.0 mL/min, detection wavelength of UV absorptiometer: 258 or 288 nm, eluent A: 0.05M aqueous acetic acid solution, eluent B: 0.05M acetic acid 100% acetonitrile solution.

Concentration gradient conditions

| Time | Eluent A | Eluent B |
| --- | --- | --- |
| 0 minute | 100% | 0% |
| 15 minutes | 100% | 0% |
| 15.1 minutes | 0% | 100% |
| 25 minutes | 0% | 100% |
| 25.1 minutes | 100% | 0% |
| 30 minutes | 100% | 0% |

The retention time of hydroxyhydroquinone: 6.8 minutes. From the area found here, the hydroxyhydroquinone content (wt. %) was determined using hydroxyhydroquinone as a standard substance. The retention time of gallic acid determined in a similar manner was 11.5 minutes.

The total amount of chlorogenic acids and the amount of hydroxyhydroquinone in the instant coffee and the fraction A prepared in Example 1(a) are shown in

TABLE 1

| | Total amount of chlorogenic acids (mg/g) | Amount of hydroxyhydroquinone (mg/g) |
| --- | --- | --- |
| Instant coffee | 54 | 0.7 |
| Fraction A | 145 | Not detected |

The amount of hydrogen peroxide in the coffee composition of the present invention was analyzed using a high sensitivity hydrogen peroxide meter, but the amount of hydrogen peroxide was not detected because it was below the detection limit. Hydrogen peroxide was analyzed in the following manner. For the measurement, "SUPER ORITECTOR MODEL 5" (product of Central Kagaku Corp.), a high sensitivity hydrogen peroxide tester, was employed. Into a reaction cell of the tester, 2 mL of a sample precisely weighed by a one-mark pipette was injected. After the reaction cell was hermetically sealed, a proper measurement range was selected and a starting switch for measurement was turned on. As soon as a beep sound indicating that the instrument is ready for measurement was confirmed, 20 μL of catalase for ORITECTOR was injected via a microsyringe and an output value was read.

The instrument was calibrated with each of 0.1, 1 and 5 mg/L hydrogen peroxide standard solutions.

For the preparation of the hydrogen peroxide standard solution, a stock solution obtained by diluting hydrogen peroxide (a 30% aqueous solution, special grade, product of Wako Pure Chemical Industries, Ltd.) with deionized water to 1,000 mg/L was used. The stock solution was diluted with an extracting solution to prepare a 5 mg/L standard solution of hydrogen peroxide. With an extracting solvent, the 5 mg/L standard solution of hydrogen peroxide was diluted further with an extracting solution to prepare 1 mg/L and 0.1 mg/L standard solutions.

The extracting solution (0.2M phosphate buffer containing 0.5% potassium bromate, pH 7.0) was prepared by dissolving 11.0 g of potassium dihydrogen phosphate (special grade), 44.8 g of disodium hydrogen phosphate 12 hydrate (special grade) and 5.0 g of potassium bromate (special grade) in deionized water to prepare a 1 L of the resulting solution precisely. When the resulting extracting solution was provided for use, a nitrogen gas was introduced into the solution for at least one hour under ice cooling in advance.

Example 2

Evaluation on Hypotensive Effect
i) Test Materials and Method
(a) Evaluation test was started after blood pressure of each of 12-week-old male spontaneously hypertensive rats (SHR) was preliminarily measured for five straight days by using a commercially available noninvasive sphygmomanometer for rats (manufactured by Softron Co., Ltd.) in order to accustom the rat to sphygmomanometric operation. These rats were all bred under conditions (breeding room in a rat region) of room temperature at 25 ±1° C., relative humidity of 55±10% and illumination for 12 hours (from 7:00 am to 7:00 pm).

Administration method and amount: In a test group, fraction A obtained by removing hydroxyhydroquinone from instant coffee was used as a material to be administered. In a control group, instant coffee was used. Fraction A and instant coffee were each dissolved in physiological saline so that the total administration amount of chlorogenic acids will be 200 mg/kg. Each of them was administered orally via an oral sonde. The dosage was 5 mL/rat.

(C) Test method: One group consisted of three to six SHR. Systolic blood pressures of the caudal artery were measured prior to oral administration and 12 hours after administration and based on them, a percent change in blood pressure after 12 hours was calculated.

(d) Statistic Treatment Method
Measurement results were indicated by mean and standard deviation. As a result of Student's t-test, the significant level was designated as 5%.
ii) Results
As is apparent from Table 2, administration of the coffee composition of the present invention brought about a marked reduction in blood pressure compared with the administration of commercially available instant coffee.

TABLE 2

| | Administered material | The number of cases | Reduction in blood pressure 12 hours after administration (%) | Standard deviation |
|---|---|---|---|---|
| Control group | Instant coffee | 3 | −5.8 | 1.1 |
| Test group | Fraction A | 6 | −14.4* | 1.4 |

*There is a significant difference at a significance level of 5% or less relative to control group.

Example 3

Evaluation of Hypotensive Effect
i) Test Materials and Method
(a) As in Example 2, 12-week-old male spontaneously hypertensive rats (SHR) was bred preliminarily.
(B) Administration Method and Amount:
Physiological saline was orally administered to a control group. An extract from raw coffee beans ("Flavor Holder FH1041", product of T. Hasegawa Co., Ltd.) having chlorogenic acids as a main component was administered to a comparison group. The extract was prepared so that its administration amount would be 300 mg/kg in terms of the total chlorogenic acid amount. In test group 1, an administration material was prepared to permit the administration of FH1041 in an amount of 300 mg/kg in terms of a total chlorogenic acid amount and the administration of hydroxyhydroquinone in an amount of 0.03 mg/kg (0.01% relative to the total chlorogenic acid amount). In test group 2, an administration material was prepared to permit the administration of FH1041 in an amount of 300 mg/kg in terms of a total chlorogenic acid amount and the administration of hydroxyhydroquinone in an amount of 0.3 mg/kg (0.1% relative to the total chlorogenic acid amount). In test group 3, an administration material was prepared to permit the administration of FH1041 in an amount of 300 mg/kg in terms of a total chlorogenic acid amount and the administration of hydroxyhydroquinone in an amount of 3 mg/kg (1% relative to the total chlorogenic acid amount). Each of them was administered orally via an oral sonde. The dosage was 5 ml/rat.

Test method: One group consisted of three SHR. Systolic blood pressures of the caudal artery were measured prior to oral administration and 12 hours after administration and based on them, a percent change in blood pressure was calculated.

(d) Statistic Treatment Method
Measurement results were indicated by mean and standard deviation. As a result of multiple comparison test (Scheffe), the significant level was designated as 5%.
ii) Results
As is apparent from Table 3, the hypotensive effect of chlorogenic acids was disturbed by the addition of hydroxyhydroquinone thereto.

TABLE 3

| | Administered material | The number of cases | Reduction in blood pressure 12 hours after administration | Standard deviation |
|---|---|---|---|---|
| Control group | Physiological saline | 3 | −2.1 | 1.1 |
| Comparison group | FH1041 | 3 | −13.8 | 1.5 |

TABLE 3-continued

|  | Administered material | The number of cases | Reduction in blood pressure 12 hours after administration | Standard deviation |
|---|---|---|---|---|
| Test group 1 | FH1041 HHQ (0.03 mg/kg) | 3 | −14.3 | 2.4 |
| Test group 2 | FH1041 HHQ (0.3 mg/kg) | 3 | −8.8* | 1.4 |
| Test group 3 | FH1041 HHQ (3 mg/kg) | 3 | −6.7* | 1.0 |

HHQ: hydroxyhydroquinone
*There is a significant difference at a significance level of 5% or less relative to control group.

Example 4

(Preparation of Canned Coffee Using the Fraction A Obtained in Example 1)

A canned coffee was prepared by dissolving 0.75 g of the fraction A in 140 mL of water, filling a can with the resulting solution, seaming the can, and subjecting the can to retort sterilization (for 10 minutes at 121° C.).

Example 5

(Preparation of Coffee Powder by Using the Fraction A Obtained in Example 1)

Coffee Powder was Prepared by Grinding the Fraction A.

Example 6

The coffee composition of the present invention was also prepared in the following manner. Preparation of coffee treated with activated carbon.

Figure 1:
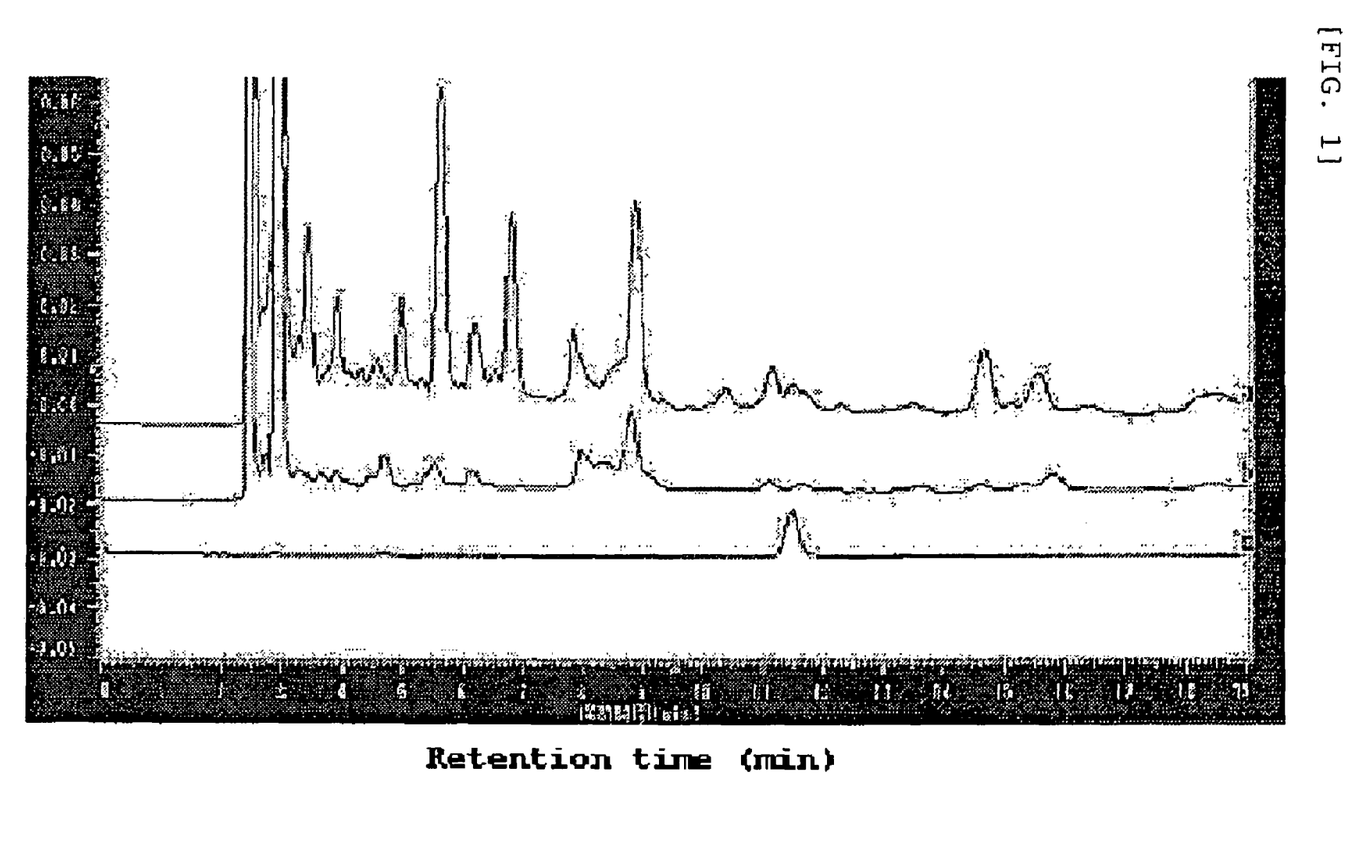
FIG. 1 illustrates an HPLC chart (detection wavelength: 258 nm) of Coffee Q.
Figure 2:
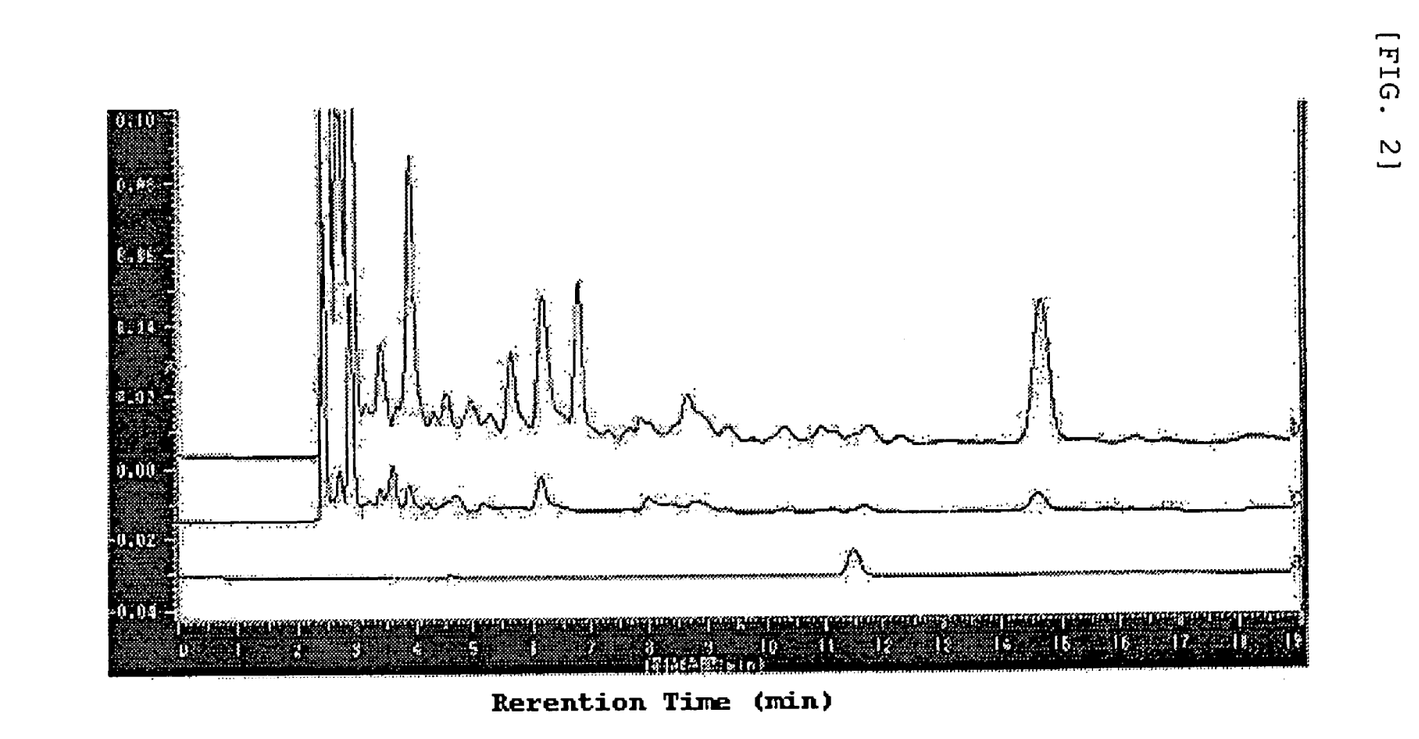
FIG. 2 illustrates an HPLC chart (detection wavelength: 288 nm) of Coffee Q.

After 20 g of commercially available instant coffee (Nescafe Gold Blend Red Label) was dissolved in 1400 mL of distilled water (which solution will hereinafter be called "Coffee P"), 30 g of activated carbon "Shirasagi $WH_2c$ 28/42" (product of Japan EnviroChemicals, Ltd., having an average pore size of 4.2 angstrom) was added to the resulting solution. The resulting mixture was stirred for one hour and then, filtered through a membrane filter (0.45 µm) to yield a filtrate (which will hereinafter be called "Coffee Q"). The resulting filtrate was freeze dried, whereby 15.8 g of brown powder was obtained. The resulting brown powder was dissolved in distilled water and amounts of chlorogenic acids and HHQ were determined by HPLC analysis as in Example 1. As a result, the chlorogenic acid content was 4.12 wt. %, while the HHQ content was below the detection limit (in accordance with the analysis conditions B). In addition, the potassium content was measured by ICP emission spectrometry. The potassium content in each of the raw material instant coffee and coffee treated with activated carbon was about. 4.2 wt. %. Analysis results of coffee P, coffee Q and gallic acid by HPLC are shown by the respective charts in FIGS. 1 and 2. In coffee Q, a peak in the vicinity of a retention time of 6.8 minutes disappears and it does not have a peak substantially. In FIG. 1, a represents the chart of coffee P, b represents the chart of coffee Q and c represents a chart of gallic acid. In FIG. 2, b represents the chart of coffee P, c represents the chart of coffee Q and a represents the chart of gallic acid.

The hydroxyhydroquinone (HHQ) content in the coffee composition of the present invention was also measured in the following manner.

Measurement of Hydroxyhydroquinone

The hydroxyhydroquinone in the coffee composition was analyzed as described below. "CoulArray System" (Model 5600A, developed and manufactured by ESA/USA, imported and sold by MC Medical Inc.), an HPLC-electrochemical detector (coulometric system) was used as an analytical instrument. The name and model number of the units constituting the instrument are as follows:

Analytical cell: "Model 5010", Coularray organizer, Coularray electronics module-software: "Model 5600A", solvent delivery module: "Model 582", gradient mixer, autosampler: "Model 542", pulse damper, degasser: "Degasys Ultimate DU3003", Column oven: 505, Column: "CAPCELL PAK C18 AQ" 4.6 mm in inner diameter×250 mm in length, particle size: 5 µm (Shiseido Co., Ltd.)

Analysis was conducted under the following conditions.

Injection amount of sample: 10 µL, flow rate: 1.0 mL/min, voltage applied to the electrochemical detector: 0 mV, set temperature of the column oven: 40° C., eluent A: 0.1 (W/V)% phosphoric acid, 0.1 mM 1-hydroxyethane-1,1-diphosphonic acid, 5 (V/V)% methanol solution, eluent B: 0.1 (W/V)% phosphoric acid, 0.1 mM 1-hydroxyethane-1,1-diphosphonic acid, 50 (V/V)% methanol solution.

For the preparation of each of eluents A and B, distilled water for high performance liquid chromatography (product of Kanto Chemical Co., Inc.), methanol for high performance liquid chromatography (product of Kanto Chemical Co., Inc.), phosphoric acid (special grade, product of Wako Pure Chemical Industries, Ltd.), and 1-hydroxyethane-1,1-diphosphonic acid (a 60% aqueous solution, product of Tokyo Chemical Industry Co., Ltd.).

Concentration Gradient Conditions

| Time | Eluent A | Eluent B |
|---|---|---|
| 0.0 minute | 100% | 0% |
| 10.0 minutes | 100% | 0% |
| 10.1 minutes | 0% | 100% |
| 20.0 minutes | 0% | 100% |
| 20.1 minutes | 100% | 0% |
| 50.0 minutes | 100% | 0% |

An analysis sample was prepared in the following manner. After 2 g of a sample was weighed precisely, the eluent A was added to give a total amount of 10 mL. The resulting mixture was filtered through a membrane filter ("HLC-DISK25 for solvents", pore size: 0.45 µm, for high performance liquid chromatography, product of Kanto Chemical Co., Inc.), and about 2.5 mL of the resulting filtrate was introduced into "Bond Elut SCX" (product of GL Science Co., Ltd., solid phase filling amount: 500 mg, reservoir capacity: 3 mL). Immediately after removal of about 0.5 mL of the initial filtrate, the residue was provided for the analysis.

In the analysis under the above-described conditions, the retention time of hydroxyhydroquinone was 6.38 minutes. From the peak area thus obtained, the content of it (wt. %) was determined using hydroxyhydroquinone (product of Wako Pure Chemical Industries, Ltd.) as a standard substance.

When the hydrogen peroxide content of the coffee composition of the present invention was measured using a high sensitivity hydrogen peroxide tester, the hydrogen peroxide content was not detected because it was below the detection limit. The ash content was measured by the above-described method, resulting in that the ash content in the coffee P was 186 mg/100 g and that in the coffee Q was 176 mg/100 g, each in terms of an amount per 100 g of coffee drink.

Example 7

After 20 g of commercially available instant coffee (Nescafe Gold Blend Red Label) was dissolved in 1400 mL of distilled water (which solution will hereinafter be called "Coffee P"), 10 g of activated carbon "Kurarycoal GW-H 48/100" (an average pore size of 3.9 angstrom) was added to the resulting solution. The resulting mixture was stirred for one hour and then, filtered through a membrane filter (0.45 µm) to yield a filtrate (which will hereinafter be called "Coffee Q"). The resulting filtrate was freeze dried, whereby 16.5 g of brown powder was obtained. The resulting brown powder was dissolved in distilled water and amounts of chlorogenic acids and HHQ were determined by HPLC.analysis as in Example 1. As a result, the chlorogenic acid content was 4.31 wt. %, while the HHQ content was below the detection limit (in accordance with the analysis conditions B). In addition, the potassium content was measured by ICP emission spectrometry. The potassium content in each of the raw material instant coffee and coffee treated with activated carbon was about 4.2 wt. %.

Example 8

Evaluation on Hypotensive Effect of Coffee Composition Prepared in Example 6

Test Materials and Method (a) Evaluation test was started after blood pressure of each of 13-to 14-week-old male spontaneously hypertensive rats (SHR) was preliminarily measured for five straight days by using a commercially available noninvasive sphygmomanometer for rats (manufactured by Softron Co., Ltd.) in order to accustom the rat to sphygmomanometric operation. These rats were all bred under conditions (breeding room in a rat region) of room temperature at 25±1° C., relative humidity of 55±10% and illumination for 12 hours (from 7:00 am to 7:00 pm).

(b) Administration method and amount: In test groups, the coffee composition (coffee treated with activated carbon) prepared in Example 6 was used. In control group, commercially available instant coffee was used. The coffee treated with activated carbon and instant coffee were each dissolved in physiological saline so that the administration amount of it would be 200 mg/kg in terms of a total chlorogenic acid amount. Each of them was administered orally via an oral sonde. The dosage was 5 mL/rat.

(c) Test method: Systolic blood pressures of the caudal artery were measured prior to oral administration and 12 hours after administration and based on them, a percent change in blood pressure after 12 hours was calculated.

(d) Statistic Treatment Method

Measurement results were indicated by mean and standard deviation. As a result of Student's t-test, the significant level was designated as 5%. Results: As is apparent from Table 4, administration of the coffee composition of the present invention brought about a marked reduction in blood pressure compared with the administration of conventional instant coffee.

TABLE 4

|  |  | The number of cases | Reduction in blood pressure 12 hours after administration | Standard deviation |
|---|---|---|---|---|
| Control group | Instant coffee | 4 | −5.1 | 1.0 |
| Test group | Fraction A | 6 | −10.0* | 0.6 |

*There is a significant difference at a significance level of 5% or less relative to control group.

Evaluation of Hypotensive Effect of the Coffee Composition Prepared in Example 6
(Evaluation of Blood Pressure Rise Suppressing Effect by Using Rats)
Test Materials and Method (a) Test animals: Evaluation test was started after blood pressure of each of 6-week-old male spontaneously hypertensive rats (SHR) was preliminarily measured for seven straight days by using a commercially available noninvasive sphygmomanometer for rats (manufactured by Softron Co., Ltd.) in order to accustom the rat to sphygmomanometric operation. These rats were all bred under conditions (breeding room in a rat region) of room temperature at 25±1° C., relative humidity of 55±10% and illumination for 12 hours (from 7:00 am to 7:00 pm).

(b) Administration method and amount: Test plots 1 and 2 and control plot were prepared. The composition was forcedly administered p.o. by using a metal gastric sonde. The dosage was 10 mL/kg/day and this amount was administered five days a week for 4 weeks.

(c) Test method: One group consisted of six to nine seven-week-old SHR. Systolic blood pressure of the caudal artery was measured prior to the test and for seven weeks after the beginning of the test.

(d) Statistic treatment method: Test results thus obtained were indicated by mean and standard deviation. As a result of Student's t-test, the significant level was designated as 5%.

Figure 3:
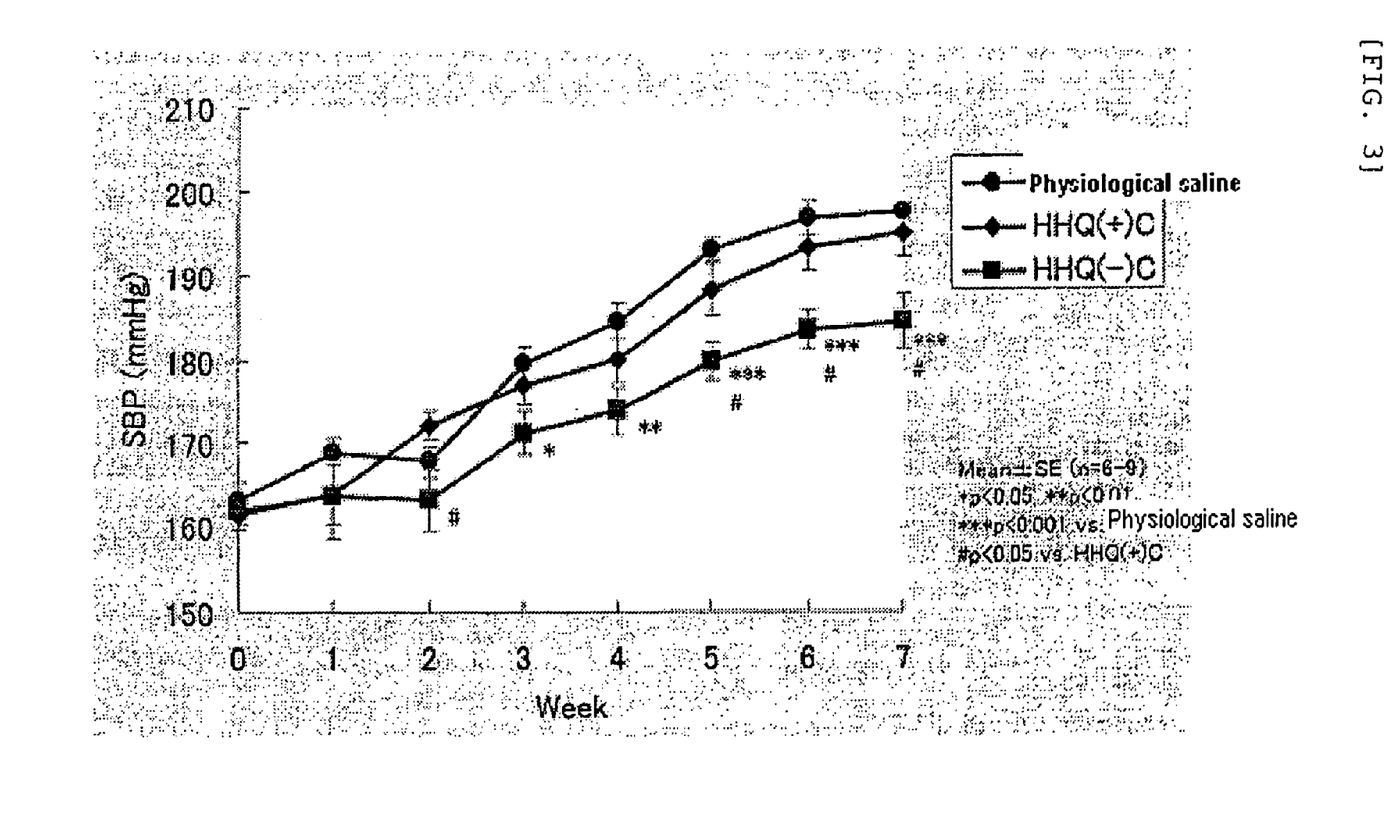
FIG. 3 illustrates a hypotensive effect of a chlorogenic-acid-removed coffee composition (HHQ(−)C) when it is administered continuously to SHR. HHQ(+)C represents a group to which non-chlorogenic-acid-removed coffee has been administered.

Results: The systolic blood pressures (SBP) before the starting of the test and for seven weeks after the starting of the test are shown in graph. As is apparent from FIG. 3, in the test plot 2 of HHQ-removed coffee, a blood pressure rise was significantly suppressed compared with that in the control plot and test plot 1.

Samples for evaluating an antihypertensive effect were prepared as described below and they were provided for a blood pressure reduction test.

Placebo (P): Hot water of 95° C. was added to 400 g of medium-roast (L=22), ground (medium ground) decaffeinated Columbia beans charged in an ordinary extractor, whereby 3200 g of an extract was obtained. Deionized water and sodium bicarbonate were added to the extract to give a pH of 6.3. The resulting mixture was filled in a metal can having a capacity of 190 g, followed by hermetic sealing. The metal can was subjected to retort sterilization at 118.1° C. for 10 minutes, whereby a test beverage for placebo was prepared. The pH after sterilization was 5.8.

Sample (S): Hot water of 95° C. was added to 400 g of medium roast (L=22) ground (medium ground) decaffeinated Columbia beans charged in an ordinary extractor, whereby 3200 g of an extract was obtained. To the extract was added 50% (w/w), relative to the solid content of the extract, activated carbon "WH2C" (product of Japan EnviroChemicals, Ltd.) and after stirring for 30 minutes, the reaction mixture was centrifuged to remove the activated carbon, whereby an HHQ-removed coffee extract was obtained. Deionized water and sodium bicarbonate were added to the extract to give a pH of 6.3. The resulting mixture was filled in a metal can having a capacity of 190 g, followed by hermetic sealing. The metal can was subjected to retort sterilization at 118.1° C. for 10 minutes, whereby a test beverage for sample was prepared. The pH after sterilization was 5.8.

(Test of Hypotensive Effect on Healthy Individuals)

Test Beverage (190 ml/can)

(P) Placebo: 433 mg/can of chlorogenic acid, 194 mg/can of caffeine, HHQ: 3.0 ppm
(S) Sample: 448 mg/can of chlorogenic acid, 142 mg/can of caffeine, HHQ: 0.1 ppm or less Test Method:

The hypotensive effect of the HHQ-removed coffee beverage was evaluated by the crossover test at intervals of 4 weeks by nine 30-to 40-year-old male volunteers.

1) Two coffee beverages, that is, the canned coffee beverage (S) which had been treated with activated carbon to remove HHQ therefrom and the ordinary canned coffee (P) were prepared. Their taste identity was confirmed. The volunteers were asked to drink a canned beverage (190 mL) every day at any time without being informed of the content of the can. They drank (P) for four weeks and (S) for four weeks, eight straight weeks in total.
2) Blood pressure measurement: The blood pressure was measured using an OMRON Blood Pressure Monitor. It was measured before drinking was started and for four weeks after drinking was started, at certain time of every week, and after ten minutes rest before measurement. The average blood pressure before the test was 138 mm Hg (systolic). The volunteers were asked not to take another coffee beverage during the test term.

Figure 4:
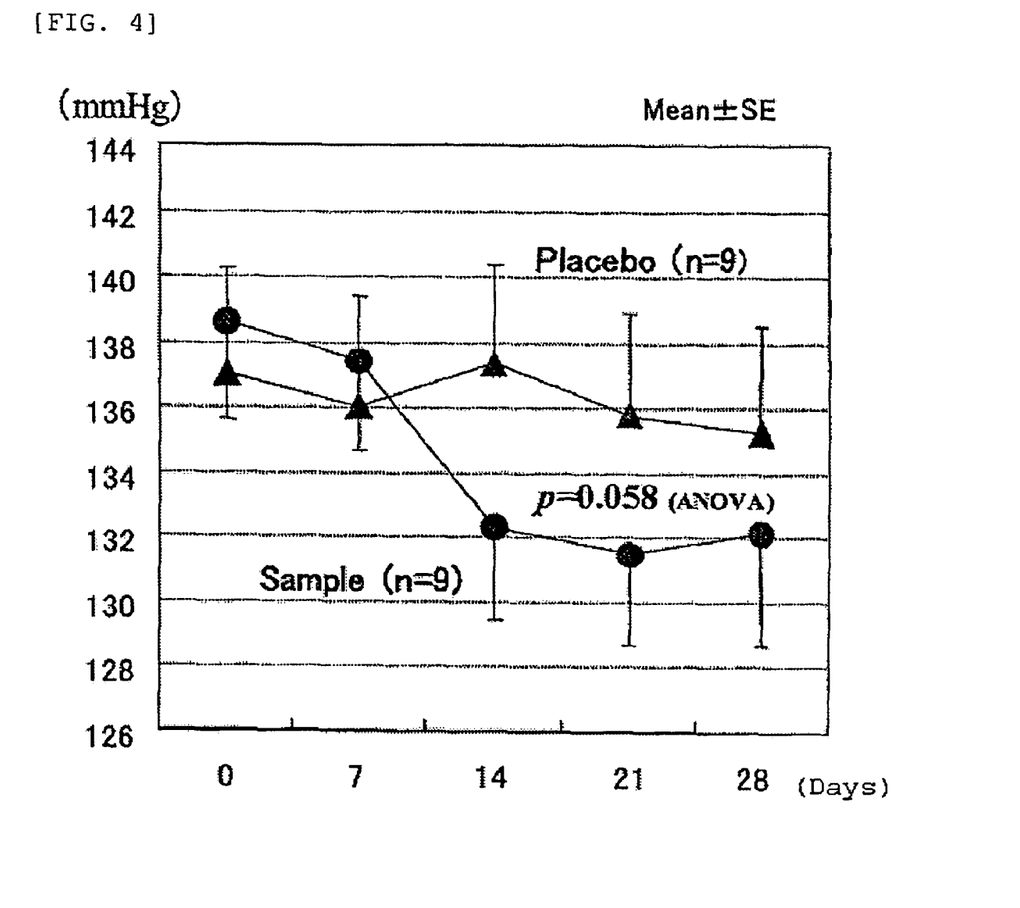
FIG. 4 illustrates an antihypertensive effect (systolic blood pressure) of a chlorogenic-acid-removed coffee composition (Sample) on humans.
Figure 5:
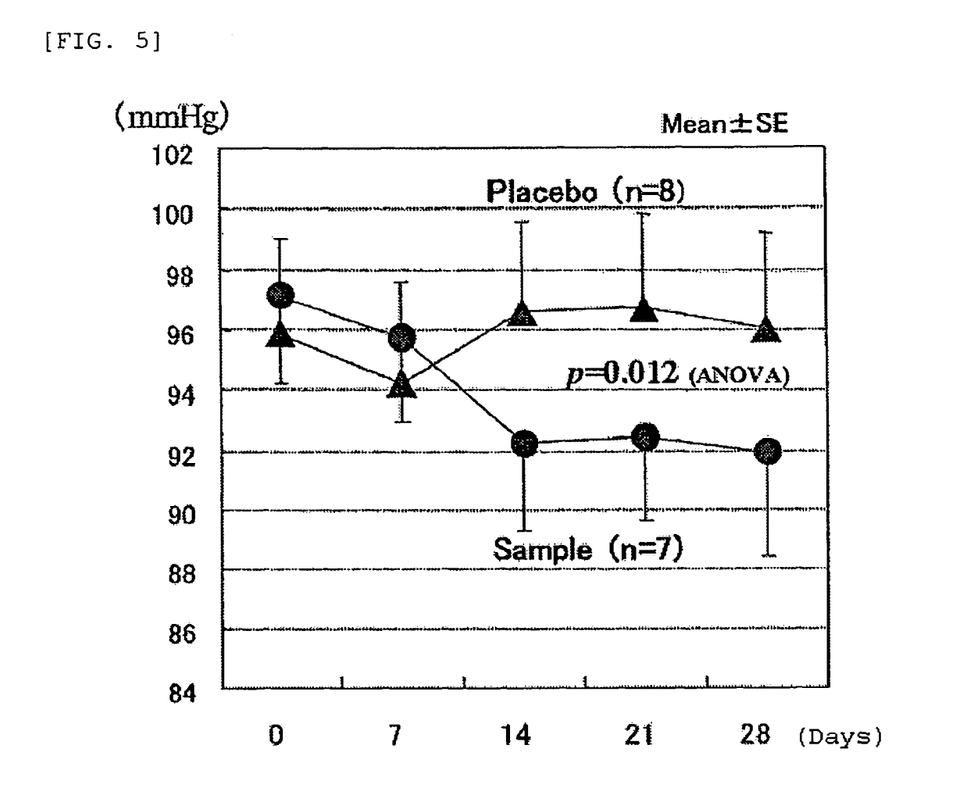
FIG. 5 illustrates an antihypertensive effect (diastolic blood pressure) of a chlorogenic-acid-removed coffee composition (Sample) on humans.

The systolic blood pressure drop after drinking is shown in FIG. 4, while the diastolic blood pressure drop after drinking is shown in FIG. 5. These diagrams show that the HHQ-removed coffee beverage of the present invention exhibited an antihypertensive effect.

Example 9

In 140 mL of water was dissolved 2 g of activated carbon-treated coffee obtained in Example 6. The resulting solution was filled in a can. The can was seamed and then subjected to retort sterilization (for 10 minutes at 121° C.), whereby a canned coffee was obtained.

Example 10

The freeze dried product obtained in Example 6 was provided as coffee powder.

Examples 11 to 13

Preparation of a Coffee Extract, Preparation of a Packaged Beverage and Evaluation of them In a multistage extractor, hot water of 120° C. was added to roasted (medium roast, L=22) and ground Guatemala coffee beans, followed by cooling, whereby a coffee extract was obtained. Relative to the amount of the beans charged in the extractor, the solid collected was 30%. To the extract was added 50% (w/w), relative to the solid content of the extract, activated carbon "WH2C" (product of Japan EnviroChemicals, Ltd.) and after stirring for 30 minutes, the reaction mixture was centrifuged to remove the activated carbon, whereby an HHQ-removed coffee extract was obtained. Deionized water and sodium bicarbonate were added to the extract to give a pH of 6.3. The resulting mixture was heated to 85° C. and then filled in a metal can having a capacity of 190 g. After the headspace was purged with $N_2$ gas, the can was seamed and hermetically sealed. The hermetically sealed can was subjected to retort sterilization at 118.1° C. for 10 minutes, whereby a packaged beverage was prepared. The pH after sterilization was 5.8. The analytical values and evaluation of the packaged beverage thus obained are shown in Table 5.

TABLE 5

| | | Example 11 CQA 100 mg/can | Example 12 CQA 300 mg/can | Example 13 CQA 800 mg/can |
|---|---|---|---|---|
| <Composition> | | | | |
| Amount of coffee extract (GUA) | Wt. % | 0.6 | 1.7 | 4.5 |
| Sodium bicarbonate | Wt. % | 0.03 | 0.10 | 0.21 |
| Deionized water | Wt. % | Balance | Balance | Balance |
| Total | Wt. % | 100 | 100 | 100 |
| <Preparation conditions> | | | | |
| Thermal sterilization conditions | | Retort | Retort | Retort |
| Container (190-mL capacity) | | Metal can | Metal can | Metal can |
| <Analysis results after sterilization> | | | | |
| Chlorogenic acids | Mg/100 g | 55.7 | 158.1 | 418.4 |
| Chlorogenic acids | Wt. % | 0.05 | 0.15 | 0.41 |
| Hydroxyhydroquinone | mg/100 g | 0.0067 | 0.019 | 0.05 |
| A ratio of hydroxyhydroquinone to chlorogenic acids | Wt. % | 0.012 | 0.012 | 0.012 |
| Existence of a peak within a range of a relative retention time of from 0.54 to 0.61 with respect to gallic acid employed as a reference substance in analysis by high performance liquid chromatography | | None | None | None |
| 4-Caffeoylquinic acid/3-caffeoylquinic acid | Weight ratio | 0.94 | 0.94 | 0.94 |
| 5-Caffeoylquinic acid/3-caffeoylquinic acid | Weight ratio | 1.01 | 1.01 | 1.01 |
| Hydroxyhydroquinone (HHQ)/total chlorogenic acid amount | Mg/100 g | 1.2/10000 | 1.2/10000 | 1.2/10000 |

TABLE 5-continued

|  |  | Example 11 CQA 100 mg/can | Example 12 CQA 300 mg/can | Example 13 CQA 800 mg/can |
|---|---|---|---|---|
| Amount of K | Mg/L | 38.8 | 110.0 | 291.1 |
| Amount of $H_2O_2$ (hydrogen peroxide in a coffee liquid just after the package is opened) |  | ND | ND | ND |
| pH |  | 5.8 | 5.8 | 5.8 |

The invention claimed is:

1. A coffee composition comprising the following components (A) and (B):
   from 0.01 to 1 wt.% of (A) chlorogenic acids,
   less than 0.1 wt.%, based on the amount of the chlorogenic acids, of (B) hydroxyhydroquinone.

2. A coffee composition comprising from 0.01 to 1 wt.% of chlorogenic acids, characterized in that in high performance liquid chromatography, the composition has no substantial peak within a range of a relative retention time of from 0.54 to 0.61 with respect to gallic acid used as a reference substance.

3. The coffee composition according to claim 1 or 2, which is a hypertension alleviating composition.

4. The coffee composition according to claim 1 or 2, which has a hypertension alleviating effect and has, attached thereto, a label indicating that the composition is useful for alleviating hypertension.

5. The coffee composition according to claim 1 or 2, which has, attached thereto, a label indicating the composition is useful for those having a higher blood pressure.

6. A soluble coffee composition comprising the following components (A) and (B):
   from 0.1 to 10 wt.% of (A) chlorogenic acids
   less than 0.1 wt.%, based on the amount of the chlorogenic acids, of (B) hydroxyhydroquinone.

7. A soluble coffee composition comprising from 0.1 to 10 wt.% of chlorogenic acids, characterized in that in high performance liquid chromatography, the composition has no substantial peak within a range of a relative retention time of from 0.54 to 0.61 with respect to gallic acid used as a reference substance.

8. The soluble coffee composition according to claim 6 or 7, which is a hypertension alleviating composition.

9. The soluble coffee composition according to claim 6 or 7, which has a hypertension alleviating effect and has, attached thereto, a label indicating that the composition is useful for reducing blood pressure.

10. The soluble coffee composition according to claim 6 or 7, which has, attached thereto, a label indicating the composition is useful for those having a higher blood pressure.

11. A packaged beverage filled with a coffee composition comprising the following components (A) and (B):
    from 0.01 to 1 wt.% of (A) chlorogenic acids
    less than 0.1 wt.%, based on the amount of the chlorogenic acids, of (B) hydroxyhydroquinone.

12. The packaged beverage according to claim 11, which is a hypertension alleviating composition.

13. The packaged beverage according to claim 11, which has a hypertension alleviating effect and has, attached thereto, a label indicating that the beverage is useful for alleviating hypertension.

14. The packaged beverage according to claim 11, which has, attached thereto, a label indicating the beverage is useful for those having a higher blood pressure.

15. The packaged beverage according to any one of claims 11 to 14, wherein the package is oxygen impermeable.

16. The process for preparing a coffee composition as claimed in any one of claims 1 to 2, which comprises treating a roasted coffee beans extract with activated carbon having an average pore size of 5 angstrom (Å) or less in a micropore region.

17. A process for preparing a soluble coffee composition as claimed in any one of claims 6 to 7, which comprises treating a roasted coffee beans extract with activated carbon having an average pore size of 5 angstrom (Å) or less in a micropore region to yield a coffee composition containing hydroxyhydroquinone in an amount less than 0.1 wt.% of the total chlorogenic acid amount; and spray drying or freeze drying the coffee composition.

* * * * *

UNITED STATES PATENT AND TRADEMARK OFFICE
CERTIFICATE OF CORRECTION

| | | |
|---|---|---|
| PATENT NO. | : 8,178,148 B2 | Page 1 of 1 |
| APPLICATION NO. | : 10/586609 | |
| DATED | : May 15, 2012 | |
| INVENTOR(S) | : Akihiko Fujii et al. | |

It is certified that error appears in the above-identified patent and that said Letters Patent is hereby corrected as shown below:

Column 1, line 45 should read:
-- Patent Document 2:JP-A-2002-87977 --

Signed and Sealed this
Tenth Day of July, 2012

David J. Kappos
*Director of the United States Patent and Trademark Office*